US006883639B1

(12) United States Patent
Lam et al.

(10) Patent No.: US 6,883,639 B1
(45) Date of Patent: Apr. 26, 2005

(54) STETHOSCOPE

(75) Inventors: Jack Lam, Taipei (TW); Yung Hsiang Chen, Taipei (TW)

(73) Assignee: Health & Life Co., Ltd., Chung-ho (TW)

( * ) Notice: Subject to any disclaimer, the term of this patent is extended or adjusted under 35 U.S.C. 154(b) by 0 days.

(21) Appl. No.: 10/715,388

(22) Filed: Nov. 19, 2003

(51) Int. Cl.[7] ............................ A61B 7/02; A61B 5/02; A61B 5/024

(52) U.S. Cl. ....................... 181/131; D24/134; 600/528

(58) Field of Search ................................ 181/131, 130, 181/129; D24/134, 106, 173, 174; 600/528; 381/67; 128/864, 867; 2/423, 209; D29/112

(56) References Cited

U.S. PATENT DOCUMENTS

| | | | | | |
|---|---|---|---|---|---|
| 585,525 | A | * | 6/1897 | Kellogg | 181/131 |
| 1,147,282 | A | * | 7/1915 | Turner | 381/67 |
| 3,288,246 | A | * | 11/1966 | Allen | 181/135 |
| 3,708,034 | A | * | 1/1973 | Ziegler et al. | 181/131 |
| 4,406,346 | A | * | 9/1983 | Pope, Jr. | 181/131 |
| 5,189,264 | A | * | 2/1993 | Peart | 181/131 |
| D335,709 | S | * | 5/1993 | Choi | D24/134 |
| 5,288,954 | A | * | 2/1994 | Peart et al. | 181/131 |
| 5,561,275 | A | * | 10/1996 | Savage et al. | 181/131 |
| D389,241 | S | * | 1/1998 | Grasfield et al. | D24/134 |
| 5,824,966 | A | * | 10/1998 | Leight | 181/130 |
| 6,056,082 | A | * | 5/2000 | Lindgren et al. | 181/130 |
| 2003/0192736 | A1 | * | 10/2003 | Werblud | 181/131 |

FOREIGN PATENT DOCUMENTS

| | | | | |
|---|---|---|---|---|
| DE | 3909011 A1 | * | 10/1989 | A61B/7/02 |

* cited by examiner

*Primary Examiner*—Edgardo San Martin
(74) *Attorney, Agent, or Firm*—Liniak, Berenato & White

(57) ABSTRACT

A stethoscope includes a pair of branches, each having a bent clip tube section with a coupling end portion connected to an ear tube section, and a curved intermediate fulcrum portion, which interconnects the coupling end portion and a resilient operating end portion and which has a concave outer surface that faces away from the other branch, and a convex inner surface that faces toward the other branch. A rubber tube is connected to the operating end portions of the clip tube sections of the branches and is in fluid communication with the branches. The intermediate fulcrum portions abut against each other. The operating end portions form a press space therebetween, and are depressible toward each other when removing the ear tube sections from the ears of the wearer.

3 Claims, 4 Drawing Sheets

20
2
221
221
20
22
22
210
2122
210
222
222
2121
212
21
211
211
213
23
20
221
221
22
22
212
211
211
21
23

STETHOSCOPE

BACKGROUND OF THE INVENTION

1. Field of the Invention

The invention relates to a stethoscope, more particularly to a stethoscope that can be worn and taken off using only one hand.

2. Description of the Related Art

Referring to FIG. 1, a conventional stethoscope is shown to include a pair of branches 10, and a Y-shaped rubber tube 11 that has a first tube section 111, and two second tube sections 112 connected to the first tube section 111. The first tube section 111 has a distal end which is connected to a chest piece (not shown). Each of the second tube sections 112 is connected to a respective one of the branches 10.

In actual use, a wearer first holds the branches 10, and then plugs or moves the branches 10 into or away from the wearer's ears using both hands. Therefore, the conventional stethoscope may result in inconvenience during use.

SUMMARY OF THE INVENTION

Therefore, the object of the present invention is to provide a stethoscope that can be worn and taken off using only one hand.

According to the present invention, a stethoscope comprises:

- a pair of branches, each of which includes
  - an elongate ear tube section having a first end adapted to be plugged into an ear of a wearer, and a second end opposite to the first end, and
  - a bent clip tube section having a coupling end portion connected to the second end of the ear tube section, a resilient operating end portion opposite to the coupling end portion, and a curved intermediate fulcrum portion interconnecting the coupling end portion and the operating end portion; and
- a rubber tube connected to the operating end portions of the clip tube sections of the branches and in fluid communication with the branches.

The intermediate fulcrum portion of the clip tube section of each of the branches has a concave outer surface that faces away from the other of the branches, and a convex inner surface that faces toward the other of the branches.

The intermediate fulcrum portions of the clip tube sections of the branches abut against each other.

The operating end portions of the clip tube sections of the branches form a press space therebetween.

The operating end portions of the clip tube sections of the branches are depressible toward each other so as to drive the ear tube sections to move from a clamping position, where the first ends of the ear tube sections of the branches are adapted to be plugged into the ears of the wearer, to a releasing position, where the first ends of the ear tube sections of the branches are moved away from the ears of the wearer.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
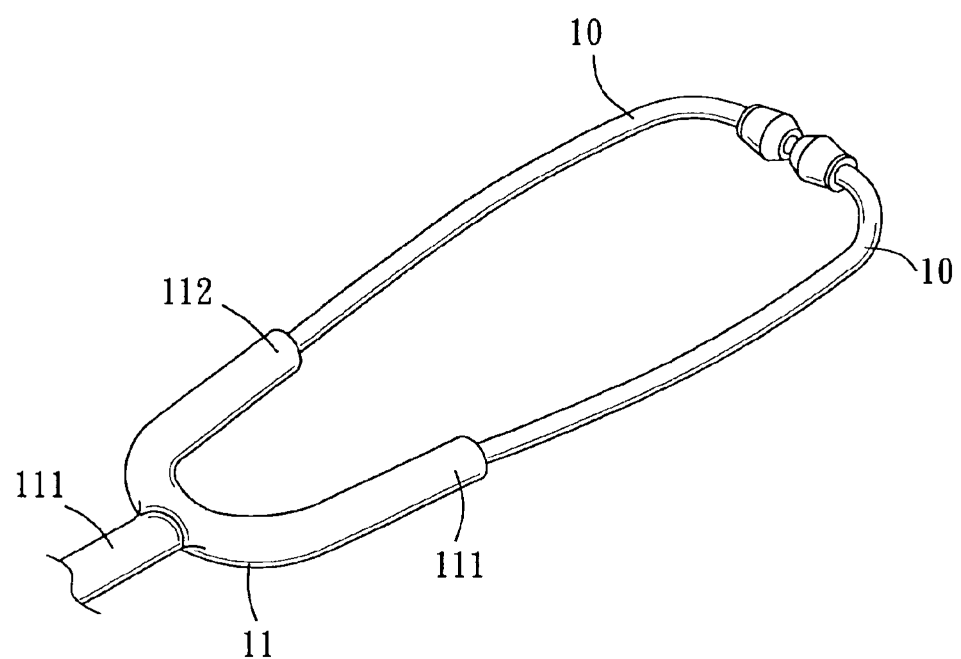
FIG. 1 is a fragmentary perspective view of a conventional stethoscope.

Before the present invention is described in greater detail, it should be noted that like elements are denoted by the same reference numerals throughout the disclosure.

Figure 2:
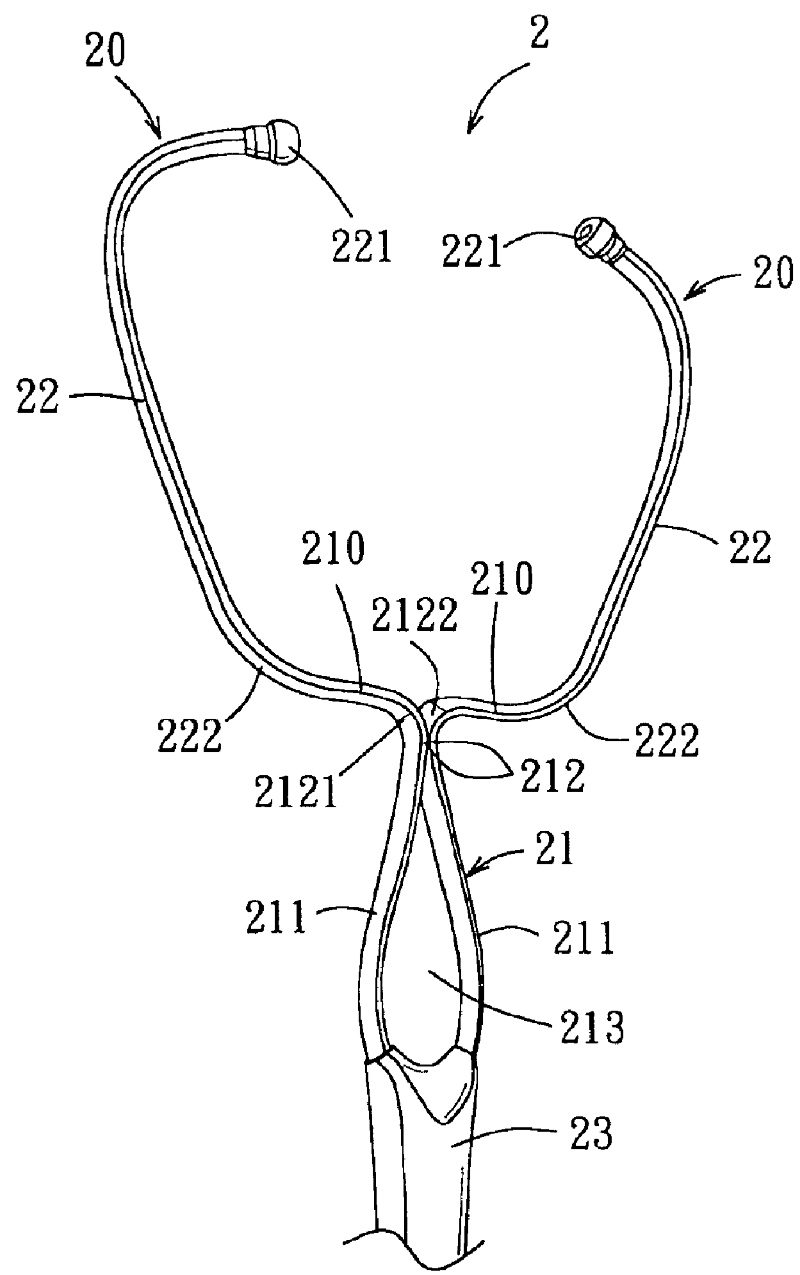
FIG. 2 is a fragmentary perspective view showing the first preferred embodiment of a stethoscope according to this invention.

Referring to FIG. 2, the first preferred embodiment of a stethoscope 2 according to the present invention is shown to include a pair of branches 20 and a rubber tube 23.

Each of the branches 20 includes an elongate ear tube section 22 and a bent clip tube section 21. The ear tube section 22 of each branch 20 has a first end 221 adapted to be plugged into an ear of a wearer (not shown), and a second end 222 opposite to the first end 221. The bent clip tube section 21 of each branch 20 has a coupling end portion 210 connected to the second end 222 of the ear tube section 22, a resilient operating end portion 211 opposite to the coupling end portion 210, and a curved intermediate fulcrum portion 212 interconnecting the coupling end portion 210 and the operating end portion 211.

The rubber tube 23 has an upper end connected to the operating end portions 211 of the clip tube sections 21 of the branches 20 and in fluid communication with the branches 20, and a lower end connected to a chest piece (not shown).

Figure 3:
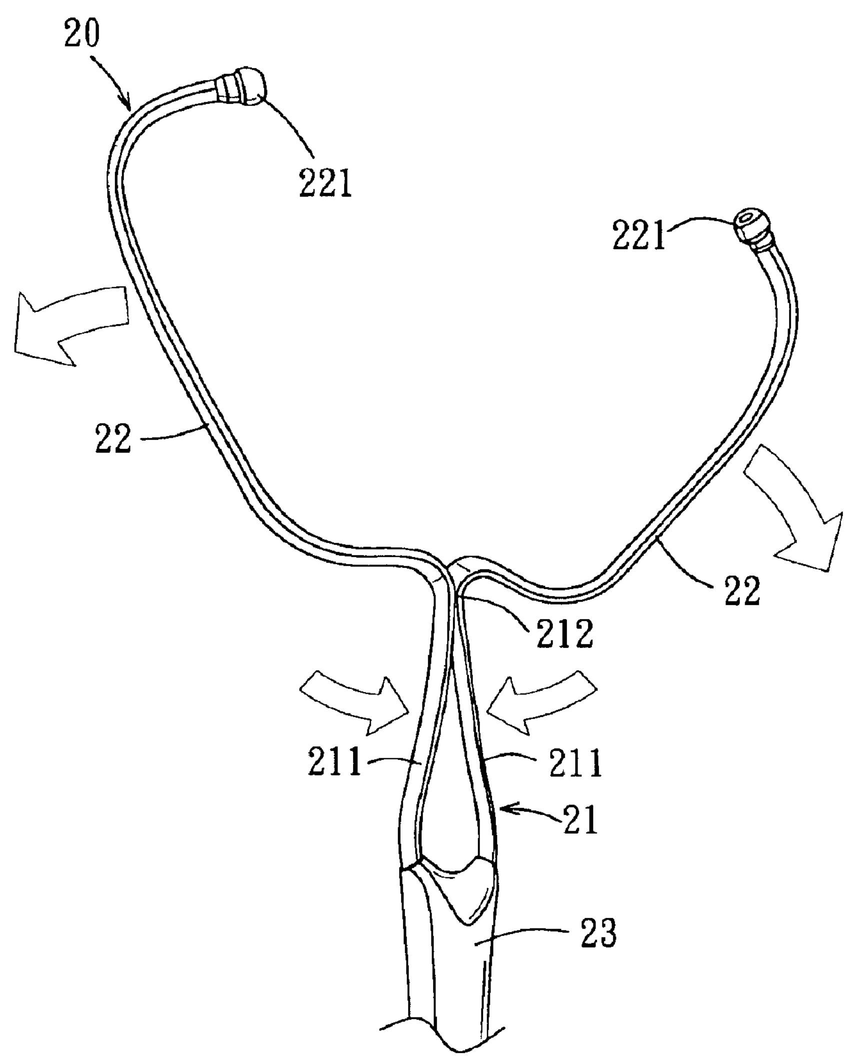
FIG. 3 is a fragmentary perspective view illustrating how ear tube sections of a pair of branches of the stethoscope of FIG. 2 are moved to a releasing position.

It is noted that the intermediate fulcrum portion 212 of the clip tube section 21 of each branch 20 has a concave outer surface 2121 that faces away from the other of the branches 20, and a convex inner surface 2122 that faces toward the other of the branches 20. The intermediate fulcrum portions 212 of the clip tube sections 21 of the branches 20 abut against each other. The operating end portions 211 of the clip tube sections 21 of the branches 20 form a press space 213 therebetween. The operating end portions 211 of the clip tube sections 21 of the branches 20 are depressible toward each other so as to drive the ear tube sections 22 to move from a clamping position, where the first ends 221 of the ear tube sections 22 of the branches 20 are adapted to be plugged into the ears of the wear, as shown in FIG. 2, to a releasing position, where the first ends 221 of the ear tube sections 22 of the branches 20 are moved away from the ears of the wearer, as shown in FIG. 3. Preferably, the intermediate fulcrum portion 212 of the clip tube section 21 of each branch 20 has a rectangular cross section such that the intermediate fulcrum portions 212 of the clip tube sections 21 of the branches 20 can have a relatively large contact area.

Figure 4:
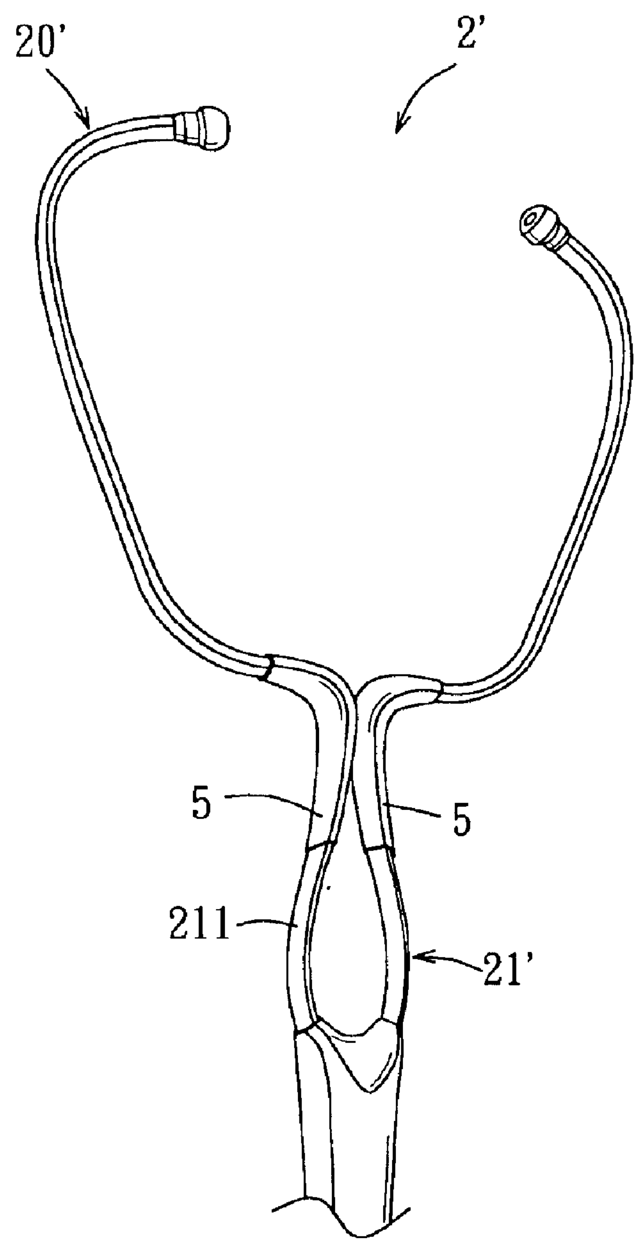
FIG. 4 is a fragmentary perspective view showing the second preferred embodiment of a stethoscope according to this invention.

FIG. 4 illustrates the second preferred embodiment of a stethoscope 2' according to this invention, which is a modification of the first preferred embodiment. In this embodiment, the intermediate fulcrum portion of the clip tube section 21' of each branch 20' has an anti-slip sleeve 5 sleeved thereon.

To sum up, the ear tube sections of the branches 20, 20' can be driven to move away from or toward each other by depressing or releasing the operating end portions 211 of the clip tube sections 21, 21' of the branches 20, 20' such that only one hand of the wearer is required when wearing and taking off the stethoscope 2, 2' of this invention.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

We claim:

1. A stethoscope comprising:

a pair of branches, each of which includes an elongate ear tube section having a first end adapted to be plugged into an ear of a wearer, and a second end opposite to said first end, and a bent clip tube section having a coupling end portion connected to said second end of said ear tube section, a resilient operating end portion opposite to said coupling end portion, and a curved intermediate fulcrum portion interconnecting said coupling end portion and said operating end portion; and a rubber tube connected to said operating end portions of said clip tube sections of said branches and in fluid communication with said branches;

said intermediate fulcrum portion of said clip tube section of each of said branches having a concave outer surface that faces away from the other of said branches, and a convex inner surface that faces toward the other of said branches;

said intermediate fulcrum portions of said clip tube sections of said branches abutting against each other;

said operating end portions of said clip tube sections of said branches forming a press space therebetween;

said operating end portions of said clip tube sections of said branches being depressible toward each other so as to drive said ear tube sections to move from a clamping position, where said first ends of said ear tube sections of said branches are adapted to be plugged into the ears of the wearer, to a releasing position, where said first ends of said ear tube sections of said branches are moved away from the ears of the wearer.

2. The stethoscope as claimed in claim 1, wherein said intermediate fulcrum portion of said clip tube section of each of said branches has an anti-slip sleeve sleeved thereon.

3. The stethoscope as claimed in claim 1, wherein said intermediate fulcrum portion of said clip tube section of each of said branches has a substantially rectangular cross section.

* * * * *